(12) United States Patent
Amoah et al.

(10) Patent No.: US 8,246,616 B2
(45) Date of Patent: Aug. 21, 2012

(54) ELECTROSURGICAL SYSTEM

(75) Inventors: Francis Amoah, Berks (GB); Michael D. Newton, Newport (GB); Richard J. Curtis, Newport (GB); Anthony M. P. Giles, Gwent (GB)

(73) Assignee: Gyrus Medical Limited, Cardiff (GB)

( * ) Notice: Subject to any disclaimer, the term of this patent is extended or adjusted under 35 U.S.C. 154(b) by 674 days.

(21) Appl. No.: 12/318,970

(22) Filed: Jan. 13, 2009

(65) Prior Publication Data

US 2009/0198225 A1 Aug. 6, 2009

Related U.S. Application Data

(60) Provisional application No. 61/006,720, filed on Jan. 29, 2008.

(30) Foreign Application Priority Data

Jan. 16, 2008 (GB) .................................. 0800772.6

(51) Int. Cl.
A61B 18/18 (2006.01)
(52) U.S. Cl. .......................................... 606/42; 606/37
(58) Field of Classification Search .................... 606/33, 606/37, 42
See application file for complete search history.

(56) References Cited

U.S. PATENT DOCUMENTS

| | | | |
|---|---|---|---|
| 5,951,545 A | 9/1999 | Schilling et al. | |
| 2004/0019347 A1 | 1/2004 | Sakurai et al. | |
| 2004/0097916 A1* | 5/2004 | Thompson et al. | 606/34 |
| 2004/0215131 A1 | 10/2004 | Sakurai | |
| 2005/0043828 A1 | 2/2005 | Tanaka et al. | |
| 2005/0143724 A1 | 6/2005 | El-Galley et al. | |
| 2006/0217700 A1* | 9/2006 | Garito et al. | 606/34 |

FOREIGN PATENT DOCUMENTS

| | | |
|---|---|---|
| WO | WO 01/37745 A1 | 5/2001 |
| WO | WO 2004/045436 A1 | 6/2004 |

OTHER PUBLICATIONS

Search Report for GB0800772.6 (Date of Search: May 16, 2008).
International Search Report issued in corresponding International Application No. PCT/GB2009/000008, mailed Apr. 6, 2009.

* cited by examiner

*Primary Examiner* — Jackie Ho
*Assistant Examiner* — Weng Lee
(74) *Attorney, Agent, or Firm* — Nixon & Vanderhye, PC

(57) ABSTRACT

An electrosurgical system includes an electrosurgical generator including at least one source of radio frequency (RF) power, and a plurality of output connections, only one of the output connections at any one time being active in that it is able to receive radio frequency power from the source. The generator includes selection means adapted to change the active output connection, and a controller adapted to control the supply of radio frequency power from the source to the active output connection. The system also includes a plurality of electrosurgical assemblies, each including an electrosurgical instrument and a cable connecting the electrosurgical instrument to one of the output connections. The electrosurgical assemblies each include a handswitch adapted to send a signal to the selection means to change the active output connection. The selection means is such that a signal sent from the handswitch of the active instrument can cause the selection means to change the active output connection to a different output connection, but a signal sent from the handswitch of an instrument other than the active instrument does not immediately cause the selection means to change the active output connection to a different output connection.

17 Claims, 3 Drawing Sheets

ELECTROSURGICAL SYSTEM

CROSS-REFERENCE TO RELATED APPLICATION

This application claims the benefit of Provisional Application No. 61/006,720 filed Jan. 29, 2008, the entire contents of which are hereby incorporated by reference in this application.

FIELD OF INVENTION

This invention relates to an electrosurgical system including an electrosurgical generator, and a plurality of electrosurgical instruments for use therewith.

BACKGROUND OF THE INVENTION

The majority of electrosurgical generators are designed to have only one instrument attached to the generator at any one time. However, there is an increasing trend, with ever more sophisticated electrosurgery systems, to have multiple instruments connected to the generator at any one time. U.S. Pat. Nos. 5,342,356 and 6,508,809 relate to two examples of electrosurgical systems in which multiple instruments can be connected to a single generator. These patent specifications describe how shaped-connectors, color-coding and distinct symbols can be used to assist with the connection of these multiple instruments, and to ensure that the correct instrument is connected to the appropriate output of the generator.

Another example of an electrosurgery system with multiple instruments connected to a single generator is described in US patent application 2004/0215131. Like most of these known electrosurgical generators, this application describes a system that only allows for the operation of one of the attached instruments at any one time. Hand switches are present on the electrosurgical instruments, and the pressing of any of the hand switches immediately makes that instrument the "active" instrument.

It is an aim of the present invention to provide an improved electrosurgical system in which various electrosurgical instruments can be selected.

SUMMARY OF THE INVENTION

The present invention provides an electrosurgical system comprising:
I) an electrosurgical generator comprising:
a) at least one source of radio frequency (RF) power,
b) a plurality of output connections, only one of the output connections at any one time being active in that it is able to receive radio frequency power from the source, and
c) means for controlling the supply of radio frequency power from the source to the active output connection; and
ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, each of the electrosurgical instruments including a hand switch adapted to change the active output connection;
the system being such that a signal sent from the hand switch of the active instrument changes the active output connection to a different output connection, but a signal sent from the hand switch of an instrument other than the active instrument does not change the active output connection to a different output connection.

For the purposes of this specification, the instrument to which electrosurgical power can be supplied is described as the "active" instrument, and that instrument is said to be in "focus". The problem with systems such as the one described in US patent application 2004/0215131 is that the transfer of focus from one instrument to another can be effected regardless of whether the instrument previously in focus has finished its work. There is, therefore, the possibility one surgeon can take control of the active output of the electrosurgical generator, before the other surgeon would like this to occur. It is frequently the case that a more experienced surgeon will work alongside a less experienced surgeon, either for training purposes or because one surgeon is pre-eminent in his or her field. It is, therefore, advantageous to give the more experienced surgeon control over the transfer of the active instrument, as opposed to the less experienced surgeon. The present invention ensures that, when this safety mode is activated, a signal sent from a non-active instrument does not immediately cause the selection means to change the active output connection.

In a preferred arrangement, the system is such that the active output connection is transferred from one output connection to another output connection on receipt of a sequence of signals from the hand switches of the electrosurgical instruments. In one arrangement, the system is such that the sequence of signals comprises a first signal from the hand switch of the active instrument, followed by a second signal from the hand switch of an instrument other than the active instrument, thereby causing the active output connection to be transferred to the instrument sending the second signal. In this way, the transfer of focus can only proceed after consent to the transfer has effectively been given from the instrument currently in focus.

Alternatively, the system is such that the sequence of signals comprises a first signal from the hand switch of an instrument other than the active instrument, followed by a second signal from the hand switch of the active instrument, thereby causing the active output connection to be transferred to the instrument sending the first signal. In this alternative protocol, consent for the transfer of focus is requested from an instrument other than the one currently in focus, and this consent is effectively given by the user of the instrument in focus prior to any transfer taking place. Whichever protocol is employed, the change in the active instrument only goes ahead when there is a positive signal from both the instrument requesting the focus, and, unlike in US 2004/0215131, also from the instrument currently in focus.

In one convenient arrangement, the hand switch of one or more of the electrosurgical instruments comprises a switch having at least first, second and third positions. Moving the switch to the first position causes the generator to supply a cutting radio frequency signal to the active output connection, while moving the switch to the second position causes the generator to supply a coagulating radio frequency signal to the active output connection. Moving the switch to the third position sends a signal to the generator, to request or give permission for the transfer of the active output to or from that instrument.

Alternatively, the hand switch of one or more of the electrosurgical instruments comprises a switch assembly comprising at least first, second and third buttons. Depressing the first button causes the generator to supply a cutting radio frequency signal to the active output connection, while depressing the second button causes the generator to supply a coagulating radio frequency signal to the active output connection. Depressing the third button sends a signal to the generator, once again to request or give permission for the transfer of the active output to or from that instrument.

The electrosurgical systems described above effectively "push" the active focus from the currently active instrument to an alternative instrument not currently in focus. The system of US 2004/0215131 effectively "pulls" the active focus from the currently active instrument to an alternative instrument not currently in focus. It is conceivable that the users of the electrosurgical system may wish to have the option to set up the operating environment with either of these arrangements, depending on the circumstances. The electrosurgical system according to the present invention can, therefore, be set to an alternative mode in which a signal sent from the hand switch of an instrument other than the active instrument does immediately change the active output connection to a different output connection.

The invention also provides an electrosurgical system comprising:
I) an electrosurgical generator comprising:
  a) at least one source of radio frequency (RF) power,
  b) a plurality of output connections, only one of the output connections at any one time being active in that it is able to receive radio frequency power from the source,
  c) hierarchy means adapted to appoint at least one of the output connections as a primary output connection, and at least one other output connection as a secondary output connection,
  d) means for controlling the supply of radio frequency power from the source to the active output connection, and
ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, an electrosurgical instrument connected to a primary output connection being designated a primary instrument, and an electrosurgical instrument connected to a secondary output connection being designated a secondary instrument, each of the electrosurgical instruments including a hand switch adapted to send a signal to the selection means to change the active output connection,
the system being such that a signal sent from the hand switch of a primary instrument changes the active output connection to a different output connection, but a signal sent from the hand switch of a secondary instrument does not immediately change the active output connection to a different output connection.

This arrangement is a variation on the "push" or "pull" modes described above, in which the ability to switch the focus of the instruments depends on the hierarchy of the instruments concerned. A primary instrument, typically designated for a more experienced surgeon, can "pull" the focus from other secondary instruments without requiring further authorization or warning. However, other secondary instruments, typically designated for less experienced surgeons or less vital types of electrosurgical instrument, can not "pull" the focus from a primary instrument without the primary instrument giving permission for said transfer, or "pushing" the focus voluntarily to the secondary instrument.

Typically, the hierarchy means is capable of receiving signals so as to change the or each primary output connection. In this way, the setup of the electrosurgical system, including which instruments are designated as primary or secondary instruments, can be flexibly changed to suit individual circumstances.

The electrosurgical system described above can conveniently be used in conjunction with indication means, as described in our co-pending application GB 0711868.0, for giving a visible indication of which instrument is in focus.

BRIEF DESCRIPTION OF THE DRAWINGS

The invention will now be described in more detail, by way of example only, with reference to the drawings, in which.

DESCRIPTION OF PREFERRED EMBODIMENTS

Figure 1:
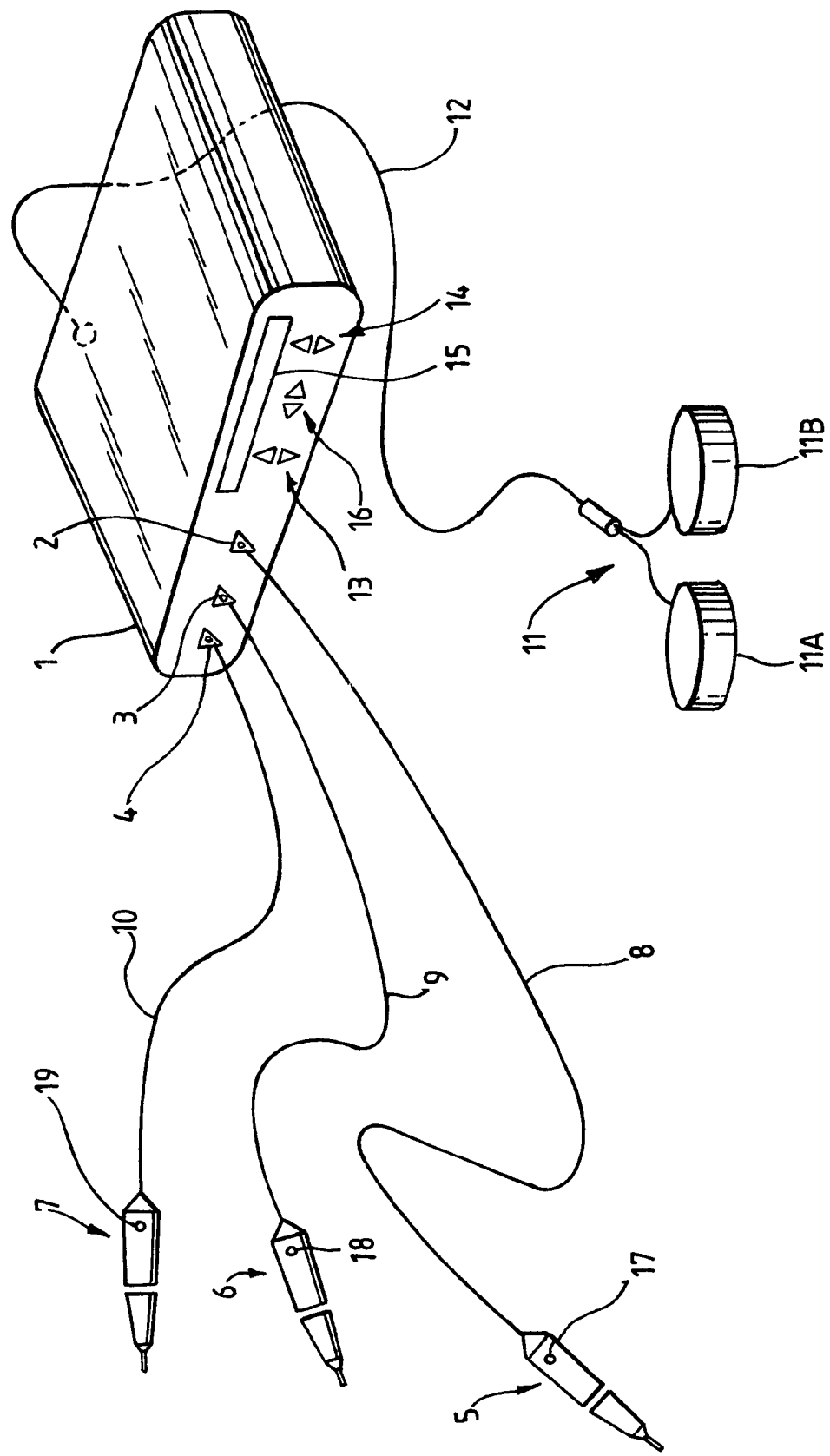
FIG. 1 is a schematic view of an electrosurgical system constructed in accordance with the invention.

Referring to FIG. 1, a generator 1 has a output sockets (connections) 2, 3, 4, providing a radio frequency (RF) output for instruments 5, 6, 7, via connection cords 8, 9, 10. Activation of the generator 1 may be performed from the instruments 5, 6, 7, via hand switches 17, 18, 19, or by means of a footswitch unit 11, as shown, connected to the rear of the generator by a footswitch connection cord 12. In the illustrated embodiment, the footswitch unit 11 has two footswitches 11A and 11B for selecting a coagulation mode and a cutting mode of the generator 1 respectively. The generator front panel has push buttons 13 and 14 for respectively setting coagulation and cutting power levels, which are indicated in a display 15. Push buttons 16 are provided as an additional means for selection between the instruments 5, 6, and 7.

Figure 2:
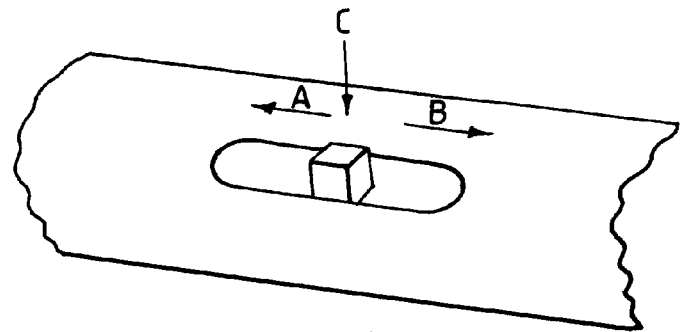
FIG. 2 is a schematic perspective view of a part of an electrosurgical instrument forming part of the system of FIG. 1.

FIG. 2 shows a typical hand switch 17 mounted on an instrument 5. The switch 17 is movable in a first direction A to send a signal to the generator 1 such that a cutting RF signal is sent to the instrument 5. Alternatively, the switch is movable in the opposite direction B to send a signal to the generator 1 such that a coagulating RF signal is sent to the instrument 5. There may additionally be other positions (not shown) into which the switch is movable, in order to obtain further variations (such as blended cut and coagulation signals etc.). However, the switch 17 may also be moved downwardly in a direction C in order to send a signal to the generator 1 to change the instrument to which the generator sends the RF signals, as will be further described below.

In use, the user selects from a menu of options whether the generator 1 is to operate in a "Push" or "Pull" mode when selecting between the instruments 5, 6 and 7. Supposing that the operator has selected the "Push" mode, one instrument 5 will be defaulted to become the initial active instrument. Thus, when the footswitch unit 11 or the hand switch 17 is activated, RF signals will be sent to the instrument 5, but not to the instruments 6 or 7. A lamp (not shown) may be illuminated on the instrument 5 to show that it has been selected as the active instrument.

If a user of the system wishes to use either of the instruments 6 and 7, one of them must be arranged to become the active instrument. As the generator 1 has been set to the "Push" mode, to do this a user must first depress the hand switch 17 on the instrument 5, to indicate that consent is given to the focus being diverted away from the instrument 5. After this signal from the instrument 5 has been received by the generator 1, if the hand switch 18 is depressed on the instrument 6, then the focus will be diverted to the instrument 6, and this instrument will become the active instrument and be ready for use. In this way, the instrument 6 does not become usable until the user of the instrument 5 has consented to the transfer. If the user of the instrument 6 depresses the hand switch 18 before the consent signal has been given from the instrument 5, the generator 1 will take no action and the focus will not be transferred.

This arrangement ensures that the user of the instrument 5 is not surprised by the transfer of focus away from the instrument 5 before the user is ready and prepared for this to occur. In a similar fashion, once the focus has been transferred to the instrument 6, the generator 1 will not transfer the focus to another instrument if a consent signal from the instrument 6 has not been received. To transfer the focus back to the instrument 5, the hand switch 18 on the instrument 6 is depressed (to provide a consent signal to the generator 1), followed by depression of the hand switch 17 on the instrument 5. A similar procedure is followed to transfer the focus to the instrument 7.

In an additional or alternative arrangement, if the active instrument is the instrument 5, and the hand switch 18 is depressed on the instrument 6 before a consent signal has been given from the instrument 5, the generator 1 sends a signal to request permission for the transfer. This may be in the form of a message displayed on the display 15, an audible tone emitted by the generator 1, or by causing a lamp (not shown) to flash on the instrument 5. If the user of the instrument 5 consents to the transfer of focus, the user depresses the handswitch 17 to send a signal to the generator 1, which then transfers the focus to make the instrument 6 the active instrument. In this way, permission can be given for the change of instrument focus, after a request from the new instrument, rather than before such a request is made.

Another way in which the generator 1 can be set up is to transfer the instrument focus in a "Pull" mode. In this way, if the handswitch 18 is depressed on the instrument 6 before a consent signal has been given from the instrument 5, the generator 1 sends a signal to transfer the instrument focus regardless of whether or not there has been a consent to the transfer from the currently active instrument. A further option is for different instruments to be given greater status than others. For example, the instrument 5 may be designated for the most senior surgeon attending the procedure, and this may be given full rights. In this way, the instrument 5 may be able to "Pull" the focus from the other instruments 6 and 7, without requiring consent to such a transfer. Furthermore, the other instruments 6 and 7 may not have equivalent rights, requiring the senior instrument 5 to "Push" the focus to them by giving consent as previously described. This arrangement is suitable for a situation in which the instrument 5 is used by an experienced senior surgeon, and the instruments 6 and 7 by less senior or less experienced colleagues.

Figure 3:
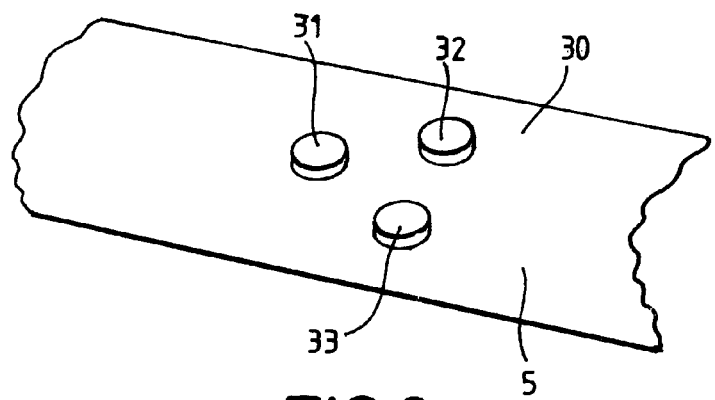
FIG. 3 is a schematic perspective view of a part of an alternative electrosurgical instrument forming part of the system of FIG. 1.

FIG. 2 shows an arrangement in which a single handswitch 17, 18 or 19 is used on each instrument 5, 6 or 7, each handswitch having multiple positions. FIG. 3 shows an alternative arrangement in which each handswitch assembly 30 comprises three handswitch buttons 31, 32 and 33 respectively. The button 31 can be used to send a signal to the generator 1 such that a cutting RF signal is sent to the instrument 5, 6 or 7. The button 32 is used to send a signal to the generator 1 such that a coagulating RF signal is sent to the instrument 5, 6 or 7. Finally, the button 33 is used to send a signal to the generator 1 to change the instrument to which the generator sends the RF signals, as previously described. An advantage of this arrangement is that the buttons 31 and 32 are isolated when the associated instrument 5, 6 or 7 is not in focus, and the operation of the buttons when the instrument 5, 6 or 7 is not in focus will not result in any RF signals being provided to the instrument. It is only when the focus has been deliberately shifted to the instrument that the operation of the buttons 31 or 32 will result in an RF signal being provided to the instrument. Inadvertent operation of the instrument is, therefore, prevented.

Figure 4:
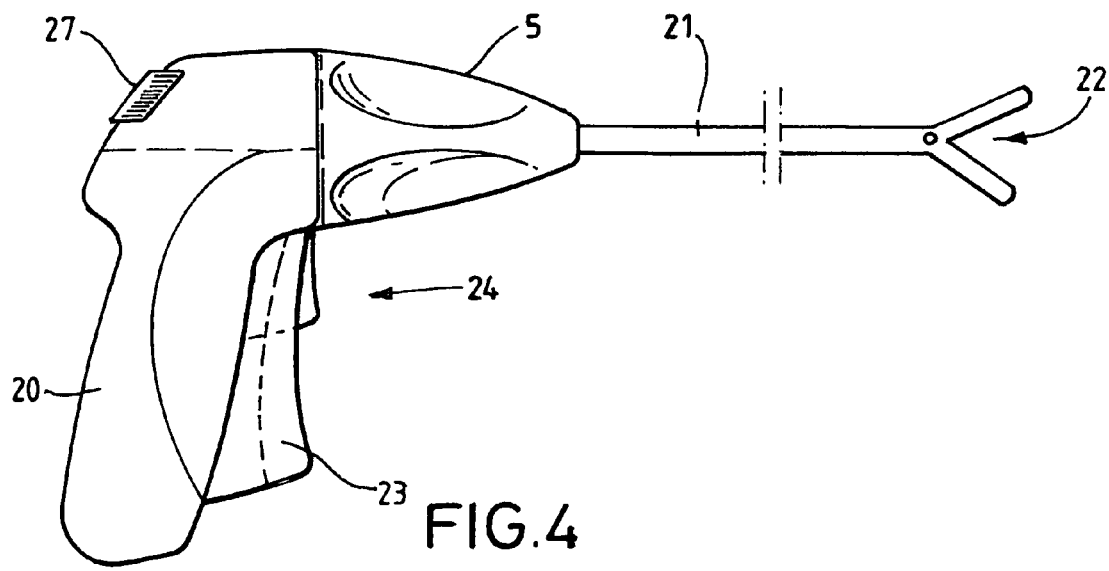
FIG. 4 is side view of an electrosurgical instrument forming part of the system of FIG. 1.

FIG. 4 shows an example of an instrument 5, such as a forceps instrument including a handpiece 20, a shaft 21 and a jawed end-effector 22 at the distal end of the shaft. An actuating handle 23 opens and closes the jaws 22, while a button 24 activates a cutting mechanism (not shown), which may either be the movement of a mechanical blade or the sending of a cutting signal to an electrosurgical cutting element. When actuation of the handle 23 has closed the jaws 22, activation of the button 24 causes the generator 1 to send a coagulating RF signal to the end-effector 22. Activation of a further handswitch 27 causes the generator 1 to send a cutting RF signal to the end-effector 22. Both the handswitches 24 and 27 are translucent and each has a lamp therein, so that when the instrument 5 is selected as the active instrument, the handswitches 24 and 27 are illuminated. Either the lamps or the translucent handswitch casings are colored, such that the coagulation handswitch 24 is illuminated with, for example, a blue color, while the cutting handswitch 27 is illuminated with for example, a yellow color.

The handswitch 27 also has a further position (a lateral movement as opposed to depressing the switch, or vice versa) that sends a signal to the generator 1 to request or consent to the transfer of focus to another instrument, or request that the focus is moved from another instrument to that instrument.

Figure 5:
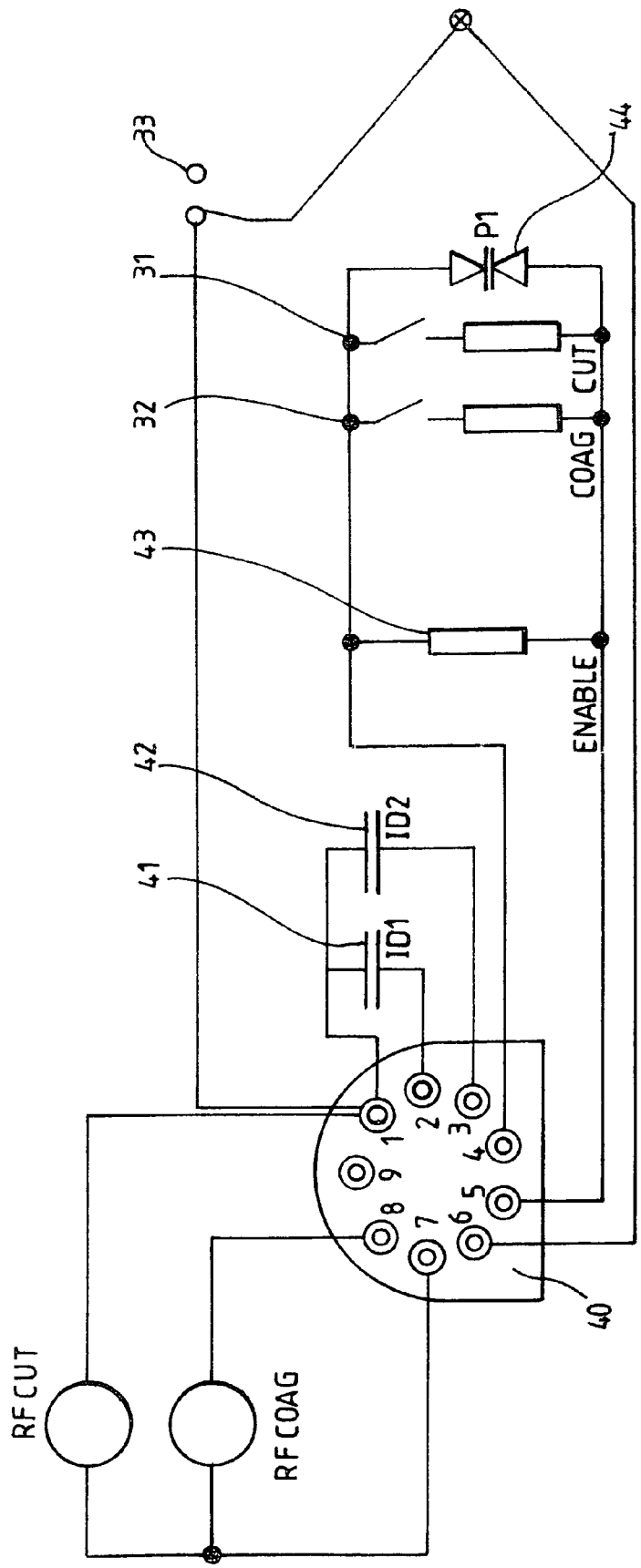
FIG. 5 is a schematic view of a circuit diagram showing the operation of the system of FIG. 1.

FIG. 5 shows a circuit diagram illustrating how the signal to request a transfer of the focus is generated. A connector 40 is shown attached to the generator 1, and includes nine pins 1 to 9. The pin 1 is an RF reference pin, completing a circuit from the pin 6, as will be described in due course. The pins 2 and 3 are connected to capacitors 41 and 42, used to identify the instrument 5 to the generator 1. The pins 4 and 5 form a circuit in which the handswitch buttons 31 and 32 are present, for coagulation and cutting respectively. Also included within this circuit are an enabling resistor 43 and a rectifier 44. The pin 6 forms, with the pin 1, a thermocouple circuit for measuring the temperature of the tip of the instrument 5, and also the button 33, for indicating or confirming a request for the transfer of the active instrument. A cutting electrode (not shown) is connected between the pin 1 and the pin 7, while a coagulating electrode (not shown) is connected to between the pin 7 and the pin 8. The pin 9 is spare.

The circuit of FIG. 5 has the advantage that, unlike the other pins, there is a current applied between the pins 6 and 1, regardless of whether the instrument 5 is currently in focus. Thus, when the switch 33 is depressed, interrupting the circuit between the pins 6 and 1, a signal can be detected by the generator 1 regardless of whether or not the instrument 5 is currently active. In this way, a signal from any of the instruments 5, 6 or 7 can be detected by the generator 1, even if only one of the instruments is in focus (or indeed even if none of the instruments is in focus). This is essential if the transfer of the focus is to be requested by a signal sent from an instrument not currently in focus. Other circuit arrangements are of course possible, but care must be taken to ensure that signals can be sent by (or detected from) instruments other that the one currently in focus. If this is not the case, it would be difficult to ensure that the transfer of focus can be effected by handswitching, as opposed to the buttons 16 present on the fascia of the generator 1.

The generator 1 includes circuitry (software plus switching relays) constituting selection means for changing which of the output connections 2, 3, 4 becomes "live". The generator 1 also includes circuitry (or possibly software control) constituting a controller for controlling the on/off supply of the RF signals to the live output connections. Finally, the generator 1 is software controlled to act as hierarchy means for determining which of the output connections 2, 3, 4 takes precedence.

What is claimed is:

1. An electrosurgical system comprising:
   i) an electrosurgical generator comprising:
      a) at least one source of radio frequency (RF) power,
      b) a plurality of output connections, only one of the output connections at any one time being active in that it is able to receive radio frequency power from the source of radio frequency power, and
      c) a controller for controlling the supply of radio frequency power from the source to the active output connection; and
   ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, each of the electrosurgical instruments including a handswitch adapted to change the active output connection;
   the system being such that the active output connection changes to a different output connection only after a signal has been sent from the handswitch of the active instrument to the generator.

2. An electrosurgical system according to claim 1, wherein the system is such that the active output connection is transferred from one output connection to another output connection on receipt of a sequence of signals from the handswitches of the electrosurgical instruments.

3. An electrosurgical system according to claim 2, wherein the system is such that the sequence of signals comprises a first signal from the handswitch of the active instrument, followed by a second signal from the handswitch of an instrument other than the active instrument, thereby causing the active output connection to be transferred to the instrument sending the second signal.

4. An electrosurgical system according to claim 2, wherein the system is such that the sequence of signals comprises a first signal from the handswitch of an instrument other than the active instrument, followed by a second signal from the handswitch of the active instrument, thereby causing the active output connection to be transferred to the instrument sending the first signal.

5. An electrosurgical system according to claim 1, wherein the handswitch of one or more of the electrosurgical instruments comprises a switch having at least first, second and third positions.

6. An electrosurgical system according to claim 5, wherein the system is such that moving said switch to the first position causes the generator to supply a cutting radio frequency signal to the active output connection.

7. An electrosurgical system according to claim 5, wherein the system is such that moving said switch to the second position causes the generator to supply a coagulating radio frequency signal to the active output connection.

8. An electrosurgical system according to claim 5, wherein the system is such that moving said switch to the third position sends a signal to the generator.

9. An electrosurgical system according to claim 1, wherein the handswitch of one or more of the electrosurgical instruments comprises a switch assembly comprising at least first, second and third buttons.

10. An electrosurgical system according to claim 9, wherein the system is such that depressing the first button causes the generator to supply a cutting radio frequency signal to the active output connection.

11. An electrosurgical system according to claim 9, wherein the arrangement is such that depressing the second button causes the generator to supply a coagulating radio frequency signal to the active output connection.

12. An electrosurgical system according to claim 9, wherein the arrangement is such that depressing the third button sends a signal to the generator.

13. An electrosurgical system according to claim 1, wherein the system is such that it can be set to an alternative mode in which a signal sent from the handswitch of an instrument other than the active instrument immediately changes the active output connection to a different output connection.

14. An electrosurgical system comprising:
   i) an electrosurgical generator comprising:
      a) at least one source of radio frequency (RF) power,
      b) a plurality of output connections, only one of the output connections at any one time being active in that it is able to receive radio frequency power from the source,
      c) hierarchy software adapted to appoint at least one of the output connections as a primary output connection, and at least one other output connection as a secondary output connection,
      d) a controller for controlling the supply of radio frequency power from the source to the active output connection, and
   ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, an electrosurgical instrument connected to a primary output connection being designated a primary instrument, and an electrosurgical instrument connected to a secondary output connection being designated a secondary instrument, each of the electrosurgical instruments including a handswitch adapted to send a signal to a selection means to change the active output connection, the system being such that a signal sent from the handswitch of a primary instrument changes the active output connection to a different output connection.

15. An electrosurgical system according to claim 14, wherein the hierarchy software is capable of receiving signals so as to change the at least one primary output connection.

16. An electrosurgical system according to claim 1, wherein a signal sent from the handswitch of an instrument other than the active instrument does not change the active output connection to a different output connection.

17. An electrosurgical system according to claim 14, wherein a signal sent from the handswitch of an instrument other than the active instrument does not change the active output connection to a different output connection.

* * * * *